(12) United States Patent
Spring

(10) Patent No.: US 8,883,178 B2
(45) Date of Patent: Nov. 11, 2014

(54) DENTAL CARE PRODUCTS WITH DIAMOND PARTICLES

(75) Inventor: Kurt Spring, Ermatingen (CH)

(73) Assignee: AMC Abrasives Marketing & Consulting LLP, London (GB)

( * ) Notice: Subject to any disclaimer, the term of this patent is extended or adjusted under 35 U.S.C. 154(b) by 151 days.

(21) Appl. No.: 13/126,398

(22) PCT Filed: Apr. 1, 2009

(86) PCT No.: PCT/EP2009/053881
§ 371 (c)(1),
(2), (4) Date: Apr. 27, 2011

(87) PCT Pub. No.: WO2010/060653
PCT Pub. Date: Jun. 3, 2010

(65) Prior Publication Data
US 2011/0262507 A1    Oct. 27, 2011

(30) Foreign Application Priority Data
Nov. 27, 2008  (EP) .................. PCT/EP2008/066334

(51) Int. Cl.
*A61K 8/02* (2006.01)
*A61Q 11/00* (2006.01)
*A46D 1/00* (2006.01)
*A61K 8/96* (2006.01)

(52) U.S. Cl.
CPC .............. *A46D 1/00* (2013.01); *A46D 1/0261* (2013.01); *A61K 8/02* (2013.01); *A61K 8/965* (2013.01); *A61Q 11/00* (2013.01); *A61K 8/0241* (2013.01); *A46B 2200/1066* (2013.01); *A46B 2200/108* (2013.01); *A61K 2800/412* (2013.01)
USPC .......................................... 424/401; 424/489

(58) Field of Classification Search
None
See application file for complete search history.

(56) References Cited

U.S. PATENT DOCUMENTS

| | | | |
|---|---|---|---|
| 3,698,388 A | | 10/1972 | Muhler |
| 4,021,263 A | * | 5/1977 | Rosenblum .................. 106/474 |
| 4,249,347 A | * | 2/1981 | Bura et al. .................... 51/298 |
| 5,094,839 A | * | 3/1992 | Lowder et al. ............... 424/49 |
| 5,908,039 A | | 6/1999 | Ochs et al. |
| 6,280,707 B1 | * | 8/2001 | Peterson et al. ............ 424/49 |
| 2002/0100491 A1 | | 8/2002 | Antler |
| 2003/0134089 A1 | * | 7/2003 | Schultz et al. .............. 428/173 |
| 2003/0165440 A1 | | 9/2003 | Roth et al. |
| 2004/0028772 A1 | * | 2/2004 | Andersen ........................ 426/3 |
| 2004/0047813 A1 | * | 3/2004 | Yano et al. .................... 424/49 |
| 2004/0161388 A1 | * | 8/2004 | Liu et al. ........................ 424/49 |
| 2005/0220829 A1 | * | 10/2005 | Sung et al. ................... 424/401 |
| 2006/0182693 A1 | | 8/2006 | Kristiansen et al. |
| 2007/0071696 A1 | * | 3/2007 | Wang et al. ................... 424/53 |
| 2007/0184121 A1 | * | 8/2007 | Sung ........................... 424/499 |
| 2007/0231245 A1 | * | 10/2007 | Kumasaka et al. .......... 423/446 |
| 2008/0131379 A1 | | 6/2008 | Kristiansen et al. |
| 2008/0193506 A1 | | 8/2008 | Kristiansen et al. |

FOREIGN PATENT DOCUMENTS

| | | |
|---|---|---|
| EP | 0109359 | 5/1984 |
| EP | 980678 | 11/1998 |
| EP | 1685875 | 8/2006 |
| FR | 2541100 | 8/1984 |
| FR | 2662937 | 12/1991 |
| GB | 1460069 | 12/1976 |
| JP | 4-243816 | 8/1992 |
| JP | 2002-129477 | 5/2002 |
| WO | 92/08437 | 5/1992 |
| WO | 2004/022018 | 3/2004 |
| WO | 2005/097045 | 10/2005 |
| WO | 2008/006725 | 1/2008 |
| ZA | 838422 | 6/1984 |

OTHER PUBLICATIONS

Buzea et al., "Nanomaterials and nano-particles: sources and toxicity", Biointerphases 2(4), Dec. 2007, American Vacuum Society, MR17-MR71.

* cited by examiner

*Primary Examiner* — Frederick Krass
*Assistant Examiner* — Isaac Shomer
(74) *Attorney, Agent, or Firm* — Shoemaker and Mattare

(57) ABSTRACT

The invention relates to a dental care product, in particular a toothpaste, comprising diamond particles. The diamond particles have sizes in a first size range from 0.3 μm to 2.5 μm, preferably from 0.5 μm to 2.0 μm, most preferably from 0.75 μm to 1.5 μm. The amount of diamond particles having sizes within the first size range is at most 2% by weight, more preferably at most 1% by weight, most preferably at most 0.5% by weight of the product. Moreover, the invention relates to a kit of parts containing a toothbrush (1) and a product as above, wherein the product is a toothpaste. The bristles (2) of the toothbrush (1) may contain abrasive particles (3), such as diamond particles. The bristles (2) may also be capable of at least temporarily retaining diamond particles.

14 Claims, 10 Drawing Sheets

DENTAL CARE PRODUCTS WITH DIAMOND PARTICLES

The present invention concerns a dental care product, in particular a toothpaste and a kit containing the dental care product and/or a tooth brush according to the independent claims.

Commonly known toothpastes, such as the one described in WO 2008/006725, comprise as major components a carrier, such as water, glycerol or polyethylene glycol, and a particulate abrasive material, such as silicas, aluminas, carbonates, or phosphates. Moreover, commonly known toothpastes may contain, among others, moisturizers, suspending agents, stabilizers, surfactants, preservatives, anti-microbial agents, anti-caries agents, anti-gingivitis agents, anti-plaque agents, anti-tartar agents, vitamins, flavor agents, coloring agents, and/or sweetening agents.

The abrasive particles contained in the toothpaste serve to remove plaque from the teeth. Typically, as in WO 2008/006725, the abrasive particles have a weight-based median particle size ranging from 1 to 30 μm and are present at from 10 to 70% by weight of the toothpaste composition. Other known toothpaste contain abrasive particles in an amount of down to 1% by weight.

However, the abrasives commonly used in toothpastes have several disadvantages. For example, these abrasive particles are usually harder than the dentin of the teeth but softer than the enamel of the teeth. Therefore, the amount of removed dental material is different for these two different parts of teeth. Moreover, abrasive particles as described in WO 2008/006725 may lead to a severe loss of tooth dentin. Exposed tooth necks are thus weakened and over-sensitive to hot-cold and/or sweet-sour influences. Furthermore, commonly known toothpastes leave a certain micro-roughness on the surface of the teeth, which results in a generally enlarged tooth surface and in a dull appearance of the teeth.

The treatment of hypersensitivity of the teeth to external thermal, chemical, or tactile stimuli is of major importance for everyday dental care. According to the commonly accepted hydrodynamic theory, hypersensitivity is attributed to movement of the dentin liquor due to the external stimuli. The dental liquor is contained in the so-called dentin tubules, which penetrate the dentin from the enamel-dentin interface to the pulp. The dental tubules usually have diameters ranging from 1 μm to 2 μm near the surface of the tooth and from 2.5 μm to 4 μm near the pulp, wherein these values depend, among others, on the age of the patient.

Commonly known treatments of hypersensitivity involve the sealing of the dental tubules by adhesives systems, which are, however, not suitable for an everyday use. Other treatments involve chlorhexidine or fluoride coatings or primers containing monomers. However, these chemicals are also not recommendable for an everyday use. Silver nitrate was also commonly used in the past but is obsolete today, since the tooth surfaces obtained an irreversible black discoloring after treatment.

Today, fluoride or strontium compounds are obtainable for home-use as ingredients in toothpastes. Moreover, positive results have been obtained by treatment with a potassium oxalate solution. In addition, medical chewing gums are known which deliver calcium and phosphate, which seal the dental tubules. Other known systems seal the dental tubules with methacrylates, the use of which in the oral cavity during an everyday use is, however, also questionable. Fluoride compounds react with the mineral content of the dentin and result in a sparingly soluble calcium fluoride. Finally, so-called "bioactive glasses" are known, which initiate a bioactive process.

However, all these treatments have a limited effect in time because of the abrasive action of common toothpastes which remove these sealings.

The application WO 2005/097045 discloses healthcare and cosmetic products, in particular toothpastes. These products contain nanodiamonds having an average size from about 0.5 nm to 50 nm, which are capable of bonding biological material, such as bacteria, proteins, DNA, and the like. However, nanodiamonds having these sizes cannot perform any useful abrasive or polishing action within a toothpaste. Additionally, due to their sizes, they can directly enter into the bloodstream, the consequences and side-effects of which can hardly be assessed. Moreover, this document discloses toothpastes having a diamond content of up to 40% by weight, which makes these products economically very unaffordable.

It is therefore an object of the present invention to overcome these disadvantages of known toothpastes. In particular, it is an object of the present invention to provide a dental care product, in particular a toothpaste, which is capable of filling the dental tubules and thereby reducing hypersensitivity without the need for any ingredients undergoing chemical and/or biological reactions. Another object is to provide a toothpaste which reduces the amount of removed dental material on the one hand and, on the other hand, reduces the micro-roughness of the surfaces of the teeth and thereby increases the gloss of the teeth and improves their overall appearance.

These and other objectives are solved by a dental care product according to the invention. The dental care product comprises diamond particles having sizes within a first size range from 0.3 μm to 2.5 μm, preferably from 0.5 μm to 2.0 μm, most preferably from 0.75 μm to 1.5 μm. According to the invention, the amount of diamond particles having sizes within the first size range is at most 2% by weight, more preferably at most 1% by weight, most preferably at most 0.5% by weight of the product.

Within the context of this application, a dental care product is to be understood as any product which is suitable for treating teeth, in particular human teeth. This treatment can be one to be performed by a professional in dentistry, i.e. by a dentist or a worker in a dental lab. Preferably, however, the product is intended for home use by an unprofessional private consumer, e.g. for his daily and/or weekly dental care. Thus, in a particularly preferred embodiment, the dental care product is a toothpaste.

Due to their sizes, the diamond particles having sizes in the first size range are capable of sealing the dental tubules over a period of several days, weeks, months, or permanently, since eventual particle loss will be replaced by new particles present in the toothpaste. Thereby, the inclusion of microscopic plaque or other detrimental agglomerations is prevented. This effect is particularly pronounced when the product is used on a regular basis, for example daily, as it is the case for a toothpaste. Therefore, the dental tubules can be sealed daily and not only a few times per year, as it would be the case with a professional dental treatment.

Preferably, the diamond particles are not agglomerated. Consequently, the diamond particles maintain their ability to fill the dental tubules without the need for an addition of a stabilizer preventing an agglomeration within the dental care product. Moreover, due to their chemical inertness, the diamond particles cannot undergo any unforeseen chemical reactions with the material of the teeth, thereby minimizing possible detrimental effects. In addition, the dental tubules of the teeth are physically/mechanically filled by the diamond particles without the need for any further chemical and/or biological reactions, such as drying and/or hardening reactions, as it is necessary, for example, when known tooth or bone replacement materials such as hydroxyl apatite are used. The filling of the dental tubules is particularly effective when the surfaces of the diamond particles have edges and corners, by which they can be anchored in the dental tubules.

Moreover, the diamond particles having sizes in the first size range are capable of removing stain and plaque and thereby effectively cleaning the teeth. Additionally, the diamond particles having sizes in the first size range can polish the surface of the teeth, i.e. significantly reduce their microroughness. Therefore, the diamond particles increase the gloss of the teeth and improve their overall appearance. Furthermore, the polished teeth surfaces offer less opportunity for attacks by plaque and bacteria. Moreover, since the sizes of the diamond particles are significantly below the sizes of common abrasive particles in dental care products, as for example toothpastes, the softer dentin necks of the teeth are not damaged by abrasion. Therefore, the diamond particles fulfill the triple function of filling the dental tubules, of removing stain and plaque, and of polishing the tooth surfaces.

In general, diamond particles are significantly harder than both the dentin and the enamel of the tooth. Therefore, an application of the product by rubbing it against the surface of the tooth leads to a more uniform removal of material of both the dentin and the enamel.

Moreover, the dental care product of the present invention, in particular the toothpaste, positively influences (i.e. reduces or removes) biofilms which are present on the surfaces of the teeth. In general, such biofilms contain a community of microorganisms such as bacteria. During the use of commonly known toothpastes, the biofilm is only removed to an unsatisfactory extent. However, due to the hardness of the diamond particles in the dental care product according to the present invention, the biofilm is more effectively removed, which decreases the risk of stain and plaque formation. This effect is particularly pronounced when the dental care product is used regularly, in particular daily and/or weekly, as it is the case for a toothpaste.

According to the present invention, the size of a diamond particle is determined as follows: The particle is imaged using a transmission electron microscope (TEM), which produces a two-dimensional image of the particle. The size of the particle is understood as the smallest diameter of a circle which contains the image of the particle, wherein the diameter of the circle is determined according to the scale of the image.

Micron and sub-micron diamond powders having such sizes can be commercially obtained from, for example, Microdiamant AG, CH-8574 Lengwil, Switzerland.

Preferably, the amount of diamond particles having sizes within the first size range is at least 0.0001% by weight, more preferably at least 0.05% by weight, most preferably at least 0.1% by weight of the product. Such an amount of diamond particles is particularly suitable for filling the dental tubules and polishing the surfaces of the teeth.

In preferred embodiments, at least 5% by weight, more preferably at least 10% by weight, more preferably at least 25% by weight of the diamond particles having sizes within the first size range have sizes within the lower half of the first size range. Diamond particles having these sizes are suitable for filling dental tubules having smaller diameters.

Moreover, with preference, at least 5% by weight, more preferably at least 10% by weight, more preferably at least 25% by weight of the diamond particles having sizes within the first size range have sizes within the upper half of the first size range. Diamond particles having these sizes are suitable for filling dental tubules having larger diameters.

Additionally, with preference, at least 2% by weight, more preferably at least 5% by weight, more preferably at least 10% by weight of the diamond particles having sizes within the first size range have sizes within the lowest quarter of the first size range.

Also, with preference, at least 2% by weight, more preferably at least 5% by weight, more preferably at least 10% by weight of the diamond particles having sizes within the first size range have sizes within the second lowest quarter of the first size range.

Moreover, with preference, at least 2% by weight, more preferably at least 5% by weight, more preferably at least 10% by weight of the diamond particles having sizes within the first size range have sizes within the second highest quarter of the first size range.

In addition, with preference, at least 2% by weight, more preferably at least 5% by weight, more preferably at least 10% by weight of the diamond particles having sizes within the first size range have sizes within the highest quarter of the first size range.

On the other hand, diamond particles having sizes below 0.2 µm may be small enough to directly enter into the bloodstream of the patient, which may lead to unforeseeable and detrimental side-effects to the patient. Thus, according to preferred embodiments, the product contains less than 0.025% by weight of, preferably less than 0.005% by weight of, more preferably no diamond particles having sizes below 0.2 µm. Also with preference, the product contains less than 0.005% by weight of, preferably less than 0.001% by weight of, more preferably no diamond particles having sizes below 0.1 µm.

The diamond particles can also serve as a stain and plaque removal substance. According to some embodiments, the toothpaste may additionally contain any other stain and plaque removal substance known in the art, as, for example, hydrated silica, silicon dioxide, zinc citrate, zinc oxide, aluminum oxide, silicon carbide, calcium carbonate, chromium dioxide, or any combinations thereof.

According to a preferred embodiment, the total amount of all diamond particles in the product (including optional diamond particles having sizes outside the size range) is less than 3% by weight, preferably less than 2.5% by weight, most preferably less than 2% by weight of the product. Quite surprisingly, even such a low percentage of diamond particles can suffice to polish the surface of the tooth to a desired extent, while at the same time, the product remains economically affordable. In spite of the rather low diamond concentrations by weight, the absolute number of individual particles with such fine particle sizes as specified above is extremely high: Each milligram of diamonds contains hundreds of millions of particles. Additionally, as has been shown by first clinical tests, patients reported that irritations of their gingiva, in particular of the epithelium of marginal and attached gingiva, decreased during even a short period in which they applied a toothpaste according to the invention. This effect is also attributed to the low content and/or the small sizes of the diamond particles in the dental care product.

In some embodiments, at least some of the diamond particles may be polycrystalline. Polycrystalline diamonds such as manufactured by Mypodiamond, Inc., Smithfield, Pa. 15478, USA, are known to provide for a better polishing action than monocrystalline diamond particles. The fraction of polycrystalline diamond particles may be chosen by a person skilled in the art according to a consideration of the acceptable costs and the results to be achieved.

In other embodiments, at least some of the diamond particles may be monocrystalline. Monocrystalline diamonds are less expensive than polycrystalline diamonds and therefore make the product more affordable. The fractions of monocrystalline diamond particles may be chosen by the person skilled in the art according to a consideration of the acceptable costs and the results to be achieved.

As opposed to monocrystalline diamond particles, polycrystalline diamond particles are black, which may lead to an unfavorable appearance if these particles filled the gaps and/or furrows of the teeth. Therefore, with preferably, at least 90% by weight of the diamond particles, more preferably at least 99% by weight of the diamond particles, most preferably all diamond particles are monocrystalline.

The dental care product may also contain a carrier substance which is known per se to a person skilled in the art, such as, for example, water, glycerol, polyethylene glycol, etc. The composition of the product may be any compound or composition according to the state of the art, with the exception of the abrasive employed.

According to a preferred embodiment, the product may contain spherical or irregularly shaped clusters comprising diamond particles.

Advantageously, the diamond particles contained in the clusters are bonded by a water soluble binder. According to preferred embodiments, the water soluble binder may comprise any of the following substances or any of their combinations:

polyvinyl alcohol (PVA, trade name Mowiol®) with all degrees of polymerization and hydrolysis of polyvinyl alcohol; polyvinyl pyrrolidone (PVP, trade names Luvitec, Luvicross, Kollidon) with all degrees of polymerization; polyvinyl pyrrolidone derivates and copolymers like polyvinyl polypyrrolidone (PVPP, trade name Crospovidon), vinylpyrrolidone vinylacetate copolymers, vinylpyrrolidone N-vinylimidazole copolymers, or vinylpyrrolidone vinylcaprolactame copolymers;

saccharides like D-glucose, D-fructose, sorbitol, and polysaccharides like starch, cellulose and pectin from all different origins and molecular weights, modified starch like acidified or basically modified starch, chemically reduced or oxidized starch, acetylated starch, hydroxypropylated starch, phosphonated starch, cellulose derivates like methyl cellulose, ethyl cellulose, hydroxyethyl methyl cellulose, hydroxypropyl cellulose, hydroxypropyl methyl cellulose, acetyl cellulose, carboxymethyl cellulose with all degrees of molecular weight and hydrolysis of cellulose and/or cellulose derivates, polyuronide like pectin or agar-agar, from all different origins and molecular weights;

gelatine from all different origins and manufacturing processes like acidic and basic processes, partially hardened gelatine from all different origins for gelatine and gelatine manufacturing processes like acidic and basic processes and different hardening substances like formaldehyde, glutaraldehyde, aluminium salts, magnesium salts, zinc salts;

naturally occurring substances with thickening behavior like alginic acid, carrageen gum, lucost bean gum (Johannisbrotkernmehl), guar gum, xanthan gum, tragacanth gum, arabic gum, karaya gum.

Preferably, the diamond particles are uniformly distributed over the entire volume of the clusters.

Clusters as herein described have a size which is reduced when they are exposed to the water which is added when the product is used, for example water from the human saliva. Therefore, the clusters containing diamond particles initially have a bigger size, which leads to a higher and faster abrasive action. During treatment of the teeth with the dental care product, in particular with the toothpaste, the binder of the clusters gradually dissolves, so that also the abrasive action is decreased. Consequently, an unintentionally long exposure of the teeth to the abrasive action is prevented.

In a preferred embodiment, the product contains clusters having sizes between 1 µm and 100 µm, preferably between 5 µm and 50 µm. According to the present invention, the size of a cluster is determined as follows: The cluster is imaged with an optical microscope, which produces a two-dimensional image of the cluster. The size of the cluster is defined as the smallest diameter of a circle which contains the image of the cluster, wherein the diameter of the circle is determined according to the scale of the image.

With preference, at least 10%, preferably at least 30%, more preferably at least 90% by weight of all diamond particles in the first size range (including optional diamond particles having sizes outside the size range) of the product are arranged in these clusters.

According to some embodiments, at least 70%, preferably at least 90%, most preferably at least 95% of the clusters contain between 40% and 60% by volume of diamond particles.

In one embodiment, the clusters are designed such that at least 90% by weight of each cluster dissolves in water within a period of 5 minutes, preferably 3 minutes, most preferably 2 minutes. These values guarantee that the abrasive action of the clusters decreases during a recommended time of teethbrushing.

In particular, the sizes of the diamond particles in the clusters and/or the composition of the water soluble binder and/or the size of the clusters is designed such that at least 90% by weight of each cluster dissolves in water within the above specified period of time.

A toothpaste according to the present invention may further contain any or all of the following components:

at least one suspending or moisturizing agent which prevents the drying-out of the toothpaste (e.g. glycerol, propylene glycol, sorbitol, or xylitol);

at least one stabilizer which prevents the precipitation of solid components and provides for a uniform consistency of the toothpaste (e.g. acacia gum, carrageenan, methylcellulose, guar gum, polyethylene glycol, potassium sorbate, propylene glycol, tragacanth gum, xanthan gum, xylose);

at least one surfactant which increases the wettability of the surface of the tooth and/or generate foam (e.g. sodium lauryl sulfate, polyethylene stearate, sodium palmitate);

at least one preservative which preserves the suspending agent and/or the stabilizer (e.g. sodium benzoate);

at least one anti-microbial agent (e.g. methylparabene);

at least one anti-caries agent (e.g. sodium fluoride, stannous fluoride);

at least one anti-gingivitis agent;

at least one anti-plaque agent (e.g. stannous fluoride);

at least one anti-tartar agent (e.g. zinc citrate, zinc chloride);

at least one vitamin;

at least one flavor agent (e.g. peppermint, spearmint, menthol, saccharin);

at least one coloring agent (e.g. aluminum silicate, barium sulfate, calcium carbonate, titanium dioxide); and/or at least one sweetening agent.

According to a preferred embodiment, the product contains at least one active ingredient which is bonded to at least a portion of the diamond particles, in particular of the diamond particles having sizes within the first size range. An active ingredient as used herein may be any substance in the product that is pharmaceutically active. In particular, the active ingredient may be chosen from the group consisting of anti-microbial agents, anti-caries agents, anti-gingivitis agents, anti-plaque agents, anti-tartar agents, vitamins, including any of the specific examples listed above, or any combinations thereof.

Preferably, the product has a Brookfield viscosity of at most 2,000,000 mPas, preferably at most 1,000,000 mPas, most preferably at most 500,000 mPas, wherein the Brookfield viscosity is measured with a Brookfield RVT viscometer using a TE spindle at 23° C. and 5 revolutions per minute. Such a viscosity is particularly useful when the product is a toothpaste, as it makes the application of the toothpaste comfortable.

According to a preferred embodiment, the product contains abrasive particles, in particular diamond particles. These abrasive particles have sizes in a second size range between 2.6 μm and 10 μm, more preferably between 3 μm and 6 μm, most preferably between 3.5 μm and 5 μm.

These abrasive particles in the second size range have the advantageous effect of making the surface of the teeth treated with the product rougher, such that the treated teeth appear to be whiter, which is a desirable cosmetic effect. In particular, the surface of the teeth is roughened in a controlled manner.

Preferably, the product contains abrasive particles having sizes in the second size range of at most 2% by weight, more preferably at most 1% by weight, most preferably at most 0.5% by weight of the product.

In general terms, the larger the diameter of the abrasive particles, the lesser the quantity of said particles should be.

In another preferred embodiment, the product contains a tooth whitening agent, preferably a chemical tooth whitening agent. This tooth whitening agent is preferably being present in an amount of less than 5%, preferably less than 2.5%, more preferably less than 1%, most preferably less than 0.1% by weight.

The tooth whitening agent in the product makes the teeth treated with the product appear to be whiter, which is a desirable cosmetic effect.

Preferably, the tooth whitening agent as described above comprises at least one of the following: hydrogen peroxide, carbamide peroxide, pentanatriumtriphosphate, polyphosphates, pyrophosphates, citric acid, papain, etc.

In some embodiments, the dental care product according to the present invention is a medical chewing gum containing abrasive particles, in particular diamond particles. Medical chewing gums as such are known in the art and are described, for example, in EP 1685875.

In other embodiments, the dental care product according to the present invention is a toothpick containing abrasive particles, in particular diamond particles. The toothpick may have shapes and dimensions as commonly known toothpicks. It may contain a core of a material which is also known from prior art, as for example, wood, plastic, or bamboo.

The abrasive particles of the toothpick may be attached to the core of the toothpick by a binder. Any known coating technique may be used for applying the binder and the diamond particles to the toothpick, in particular coating techniques which are commonly applied in the production of so-called coated abrasives which are known in the abrasive industry. By way of example, dip coating, spray coating, or transfer coating, such as with coating rollers, may be employed.

Preferably, the binder is insoluble in water and/or saliva. It may be chosen from the group consisting of polyesters, polyamides, polyacrylics, polymethacrylics, polyimides, polyetheretherketones, polyphenylsulfids, polyethylenes, polypropylenes, polystyrenes, polycarbonates, polyacrylnitrils, polyalkyds, polyvinyl butyrates, epoxies, crosslinked polyvinyl alcohols or water insoluble types with higher grade of polymerization or low grade of hydrolysis, hardened or crosslinked gelatine, polyphenol resoles, polymelaminic resoles, aliphatic hydrocarbons (with a melting temperature above 25° C., such as paraffin), olefinic, unsaturated hydrocarbons, polyolefins, waxes (vegetable, animal or synthetic compositions essentially consisting of esters and fatty acids with long-chain, aliphatic, primary alcohols), alkyd resins (strongly hydrophobic, synthetic polymers of polyvalent alcohols and multi-proton acids or fatty acids), or any combinations thereof.

In a preferred embodiment, the abrasive particles are essentially located at a tip of the toothpick, which is intended for entering between the teeth.

In further embodiments, the dental care product of the present invention is dental floss containing abrasive particles, in particular diamond particles. Dental floss per se and its production are known from the state of the art, as for example from EP 980 678, which is hereby incorporated by reference. The dental floss may contain a core of a multifilament yarn.

In preferred embodiments, the abrasive particles may be attached to the core of the dental floss by a binder, as for example a binder chosen from the group consisting of polyesters, polyamides, polyacrylics, polymethacrylics, polyimides, polyetheretherketones, polyphenylsulfids, polyethylenes, polypropylenes, polystyrenes, polycarbonates, polyacrylnitrils, polyalkyds, polyvinyl butyrates, epoxies, crosslinked polyvinyl alcohols or water insoluble types with higher grade of polymerization or low grade of hydrolysis, hardened or crosslinked gelatine, polyphenol resoles, polymelaminic resoles, aliphatic hydrocarbons (with a melting temperature above 25° C., such as paraffin), olefinic, unsaturated hydrocarbons, polyolefins, waxes (vegetable, animal or synthetic compositions essentially consisting of esters and fatty acids with long-chain, aliphatic, primary alcohols), alkyd resins (strongly hydrophobic, synthetic polymers of polyvalent alcohols and multi-proton acids or fatty acids), or any combinations thereof.

In yet another embodiment, the dental care product may be an interdental brush. In preferred embodiments, the abrasive particles may be attached to the interdental brush by any suitable binder, such as any of those listed above. Usually, interdental brushes are not recommended for a use in conjunction with commonly known toothpastes, since due to the sizes of the abrasive particles contained in these toothpastes, the interdental spaces would be damaged. However, the interdental brush may be used in conjunction with a dental care product, in particular a toothpaste according to the invention, since the diamond particles in these toothpastes are much smaller, so that the interdental spaces are treated much more gently.

A further aspect of the invention is the use of diamond particles having sizes within the size range for the production of a dental care product as described above.

Another aspect of the invention relates to a kit of parts containing a toothbrush and a dental care product as described above, wherein the product is a toothpaste. The toothbrush of the kit may be employed to apply the toothpaste to a tooth or teeth, in particular to a human tooth or teeth. In particular, the toothbrush may be a purely manual toothbrush, an electrical toothbrush, or a sonic toothbrush.

In some embodiments, the toothbrush may be any conventionally known toothbrush. In other embodiments, the toothbrush may have some or all of the properties described below.

In one embodiment, the toothbrush comprises bristles which comprise abrasive particles. The abrasive particles may be arranged only on the surface of the bristles. The abrasive particles will be only released when the toothbrush is used together with the toothpaste of the kit, either by mechanical abrasion and/or by physical or chemical action. Particularly, these abrasive particles may be diamond particles. Optionally, the abrasive particles may be also arranged in the interior of the bristles.

In a preferred embodiment, the bristles comprise abrasive particles having sizes between 0.3 µm and 50 µm, preferably between 0.4 µm and 20 µm, most preferably between 0.5 µm and 10 µm.

According to further preferred embodiments, the total amount of the abrasive particles of the bristles is less than 70% by volume, preferably less than 50% by volume, most preferably less than 30% by volume of the bristles.

According to a preferred embodiment, the abrasive particles of the bristles are essentially located on the surfaces of the bristles. Thus, essentially all abrasive particles of the bristles can get into contact with a tooth which is treated with the toothbrush.

The diamond particles are bonded to the bristles by coating technologies known in the art. Preferably a coating mixture comprising a binder and diamond particles is used for this purpose. Alternatively a binder may be applied on the bristles as a powder by any known powder coating technology. For both the liquid and the powder coating the coating mixtures contain the diamond particles and a binder. Preferably the binder is not soluble in water or any ingredients of human saliva, and may be chosen from the group consisting of polyesters, polyamides, polyacrylics, polymethacrylics, polyimides, polyetheretherketones, polyphenylsulfids, polyethylenes, polypropylenes, polystyrenes, polycarbonates, polyacrylnitrils, polyalkyds, polyvinyl butyrates, epoxies, crosslinked polyvinyl alcohols or water insoluble types with higher grade of polymerization or low grade of hydrolysis, hardened or crosslinked gelatine, polyphenol resoles, polymelaminic resoles, or any combinations thereof.

According to a further preferred embodiment, the bristles of the toothbrush are capable of retaining diamond particles contained in the toothpaste. In particular, the surfaces of the bristles may be designed such that diamond particles may be retained mechanically, as for example by friction. Accordingly, diamond particles which are originally contained in the toothpaste may be temporarily or permanently embedded in the surface of the bristles which have been brought into contact with the surface of the tooth even when the toothpaste has already been diluted by saliva. Moreover, some of the abrasive particles originating from the toothpaste may be retained in the bristles until a subsequent treatment. Thus, once the bristles of the toothbrush have been charged with abrasive particles originating from the toothpaste according to the invention, the toothbrush may be used with another toothpaste, which contains a lower content of diamond particles.

Preferably, at least a portion of the surface of at least some of the bristles is textured in such a way that the bristles are capable of retaining diamond particles contained in the toothpaste. Preferably, the texture has a surface roughness $R_{max}$ between 0.3 µm and 2.5 µm, preferably between 0.5 µm and 2.0 µm, more preferably between 0.75 µm and 1.5 µm. Moreover, preferably, the mean peak spacing according to ISO 4287 is adapted to the sizes of the diamond particles to be retained. In particular, the mean peak spacing may be in the range from 0.3 µm to 2.5 µm, preferably from 0.5 µm to 2.0 µm, more preferably from 0.75 µm to 1.5 µm.

In a preferred embodiment, the entire surface of the bristles is textured. The diamond particles may be mechanically retained by the bristles by friction, in particular by entering into recesses of the surface and by being clamped between neighboring elevations of the surface due the elasticity of the material of the bristles.

In some embodiments, at least a portion of the surface of the bristles is roughened, whereby a texture is obtained. The bristles may be roughened by processes which are known per se, such as by sand blasting.

In other embodiments, at least a portion of the surface of the bristles is porous, whereby a texture is obtained. Preferably, the entire bristles are made from a porous material, such as polyamides or polyesters, which has been subject to a heat treatment.

A further aspect of the invention relates to a kit of parts containing a first dental care product as described above comprising abrasive particles of a first size range. These abrasive particles are in particular diamond particles. Additionally, the kit of parts contains a second dental care product as described above comprising abrasive particles of a second size range and/or a tooth whitening agent. The abrasive particles of the second dental care product are in particular diamond particles.

The term "and/or" has the meaning that the second dental care product comprises abrasive particles in the second size range and no tooth whitening agent, or the second dental care product comprises no abrasive particles in the second size range and a tooth whitening agent, or the second dental care product comprises abrasive particles in the second size range and a tooth whitening agent.

These two dental care products may be e.g. contained in different toothpastes as part of the kit, one of which intended for daily use and the other one intended for weekly use. Other regimen of use of both dental care products of the kit are also possible, e.g. alternating use on a daily basis of both dental care products.

The kit of parts may be e.g. a box containing said toothpastes which can be sold to be shipped to a consumer or sold for pick-up in a shop by a consumer. Furthermore, the kit of parts may be sold over the internet, whereas the toothpastes contained in the kit can be chosen e.g. by the consumer and which are then shipped as a kit of parts to the consumer.

Moreover, the present invention is concerned with a toothbrush, in particular a purely manual toothbrush, an electrical toothbrush, or a sonic toothbrush. The toothbrush may have any or all of the properties of the toothbrush contained in the kit as described above. In particular, the toothbrush may comprise bristles comprising abrasive particles, in particular diamond particles. The abrasive particles of the bristles may be essentially located on the surfaces of the bristles. Furthermore, the abrasive particles may have sizes between 0.3 µm and 50 µm, preferably between 0.4 µm and 20 µm, most preferably between 0.5 µm and 10 µm.

Additionally or alternatively, the toothbrush may be capable of at least temporarily retaining diamond particles having sizes between 0.3 µm and 2.5 µm, preferably between 0.5 µm and 2.0 µm, more preferably between 0.75 µm and 1.5 µm.

A toothpaste containing a dental care product as described above may be directed at the use by children. This toothpaste for children preferably contains at least diamond particles with an average particle size of 0.5 µm in an amount of 0.1% by weight of the product. This toothpaste for children contains preferably fluorine in an amount of less than 1000 ppm, i.e. 1000 parts per million, more preferably of less than 500 ppm.

A toothpaste containing a dental care product as described above may be directed at the use by adults. This toothpaste for adults preferably contains at least diamond particles with an average particle size of 1 µm in an amount of 0.2% by weight of the product. This toothpaste for adults contains preferably fluorine in an amount of less than 3000 ppm, more preferably of less than 1500 ppm, most preferably between 800 ppm and 1500 ppm.

A toothpaste containing a dental care product as described above may be directed at the use as a special toothpaste. This toothpaste for special use preferably contains at least diamond particles with an average particle size of 1 µm in an amount of 0.1% by weight and with an average particle size of 4 µm in an amount of 0.1% by weight of the product. This toothpaste may contain fluorine in an amount as described for the toothpaste for children or adults or may contain no substantial amount of fluorine.

A further aspect of the present invention relates to a dental care product as described above for use in the treatment of at least one bleached tooth.

After bleaching of a tooth with conventional methods, e.g. with bleaching gels whitening the tooth chemically, the tooth often becomes hypersensitive to external thermal, chemical or tactile stimuli. Treatment of said bleached tooth significantly reduces this hypersensitivity. This is achieved by sealing the dental tubules.

Yet another aspect of the present invention relates to a method for the treatment of at least one bleached tooth with a dental care product as described above, wherein the at least one tooth is treated with the dental care product subsequently to the bleaching.

The invention will now be explained in more detail by non-limiting examples and figures, wherein FIGS. 1a,b show abrasive particles of a known toothpaste;

FIGS. 2a,b show diamond particles of a toothpaste according to the invention;

Figure 7A:
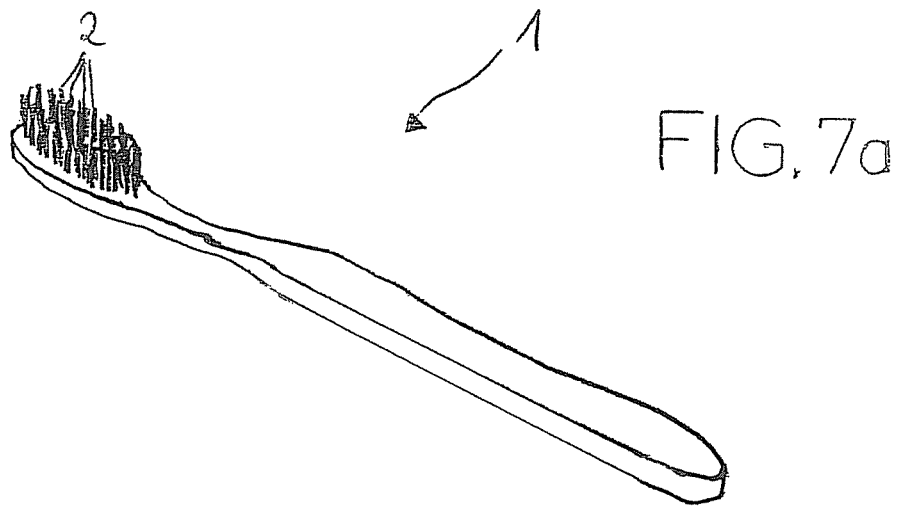
Figure 8A:
Figure 8B:
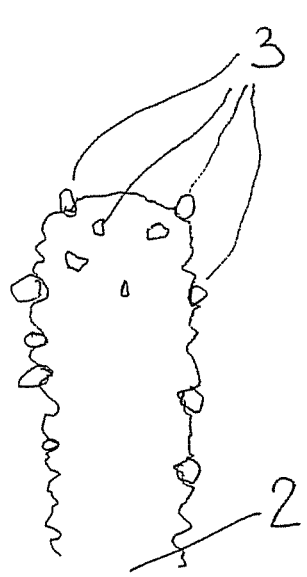
Figure 8C:
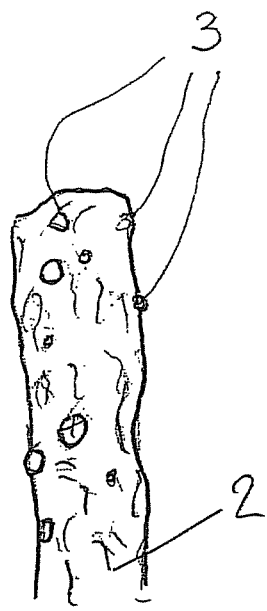

FIGS. 7a,b show a toothbrush of a kit according to the invention, wherein the toothbrush contains bristles 2 comprising abrasive particles;

FIGS. 8a-c show another toothbrush of a kit according to the invention, wherein the surfaces of the bristles are roughened and capable of retaining abrasive particles.

Figure 9:
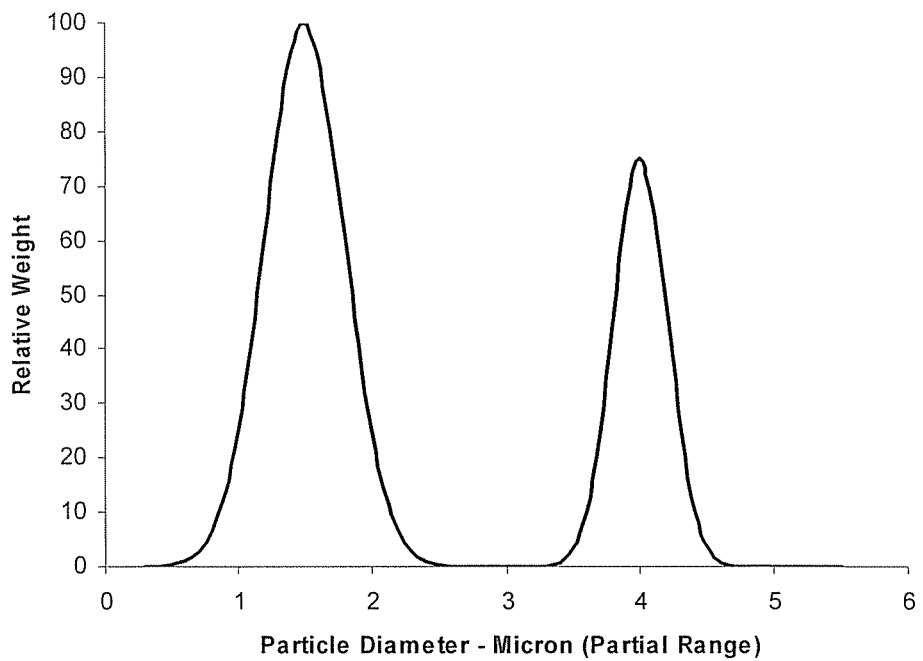
Figure 10:
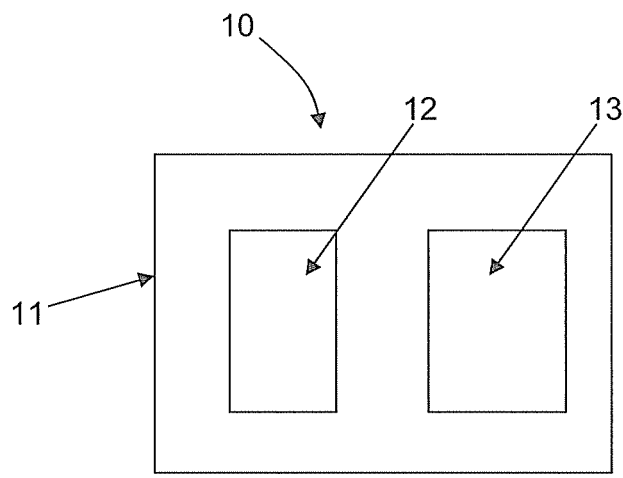

FIG. 9 shows the particle size distribution of diamond particles of a further toothpaste according to the invention FIG. 10 shows a kit of parts containing a first and second dental product according to the invention.

Figure 1A:
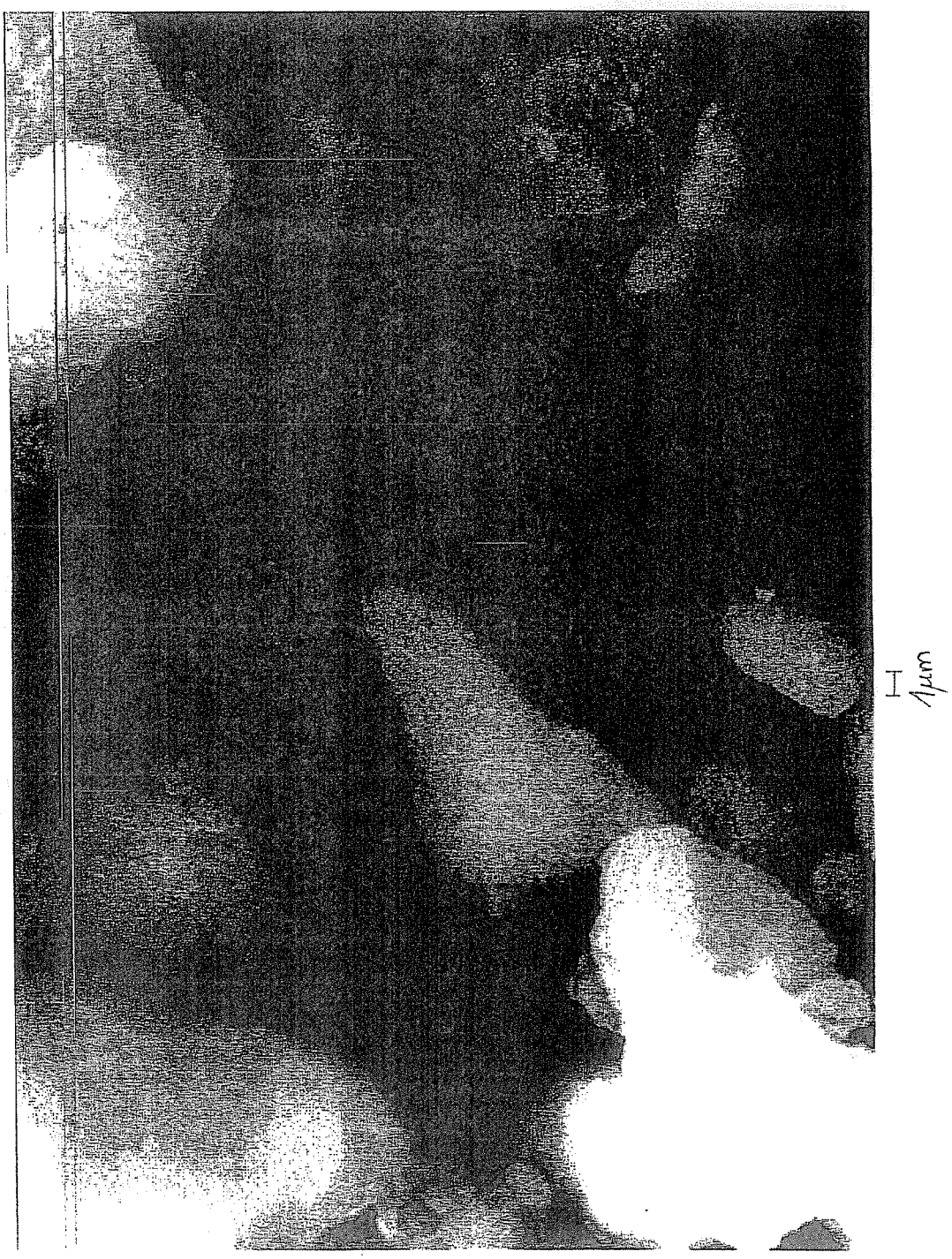
Figure 1B:
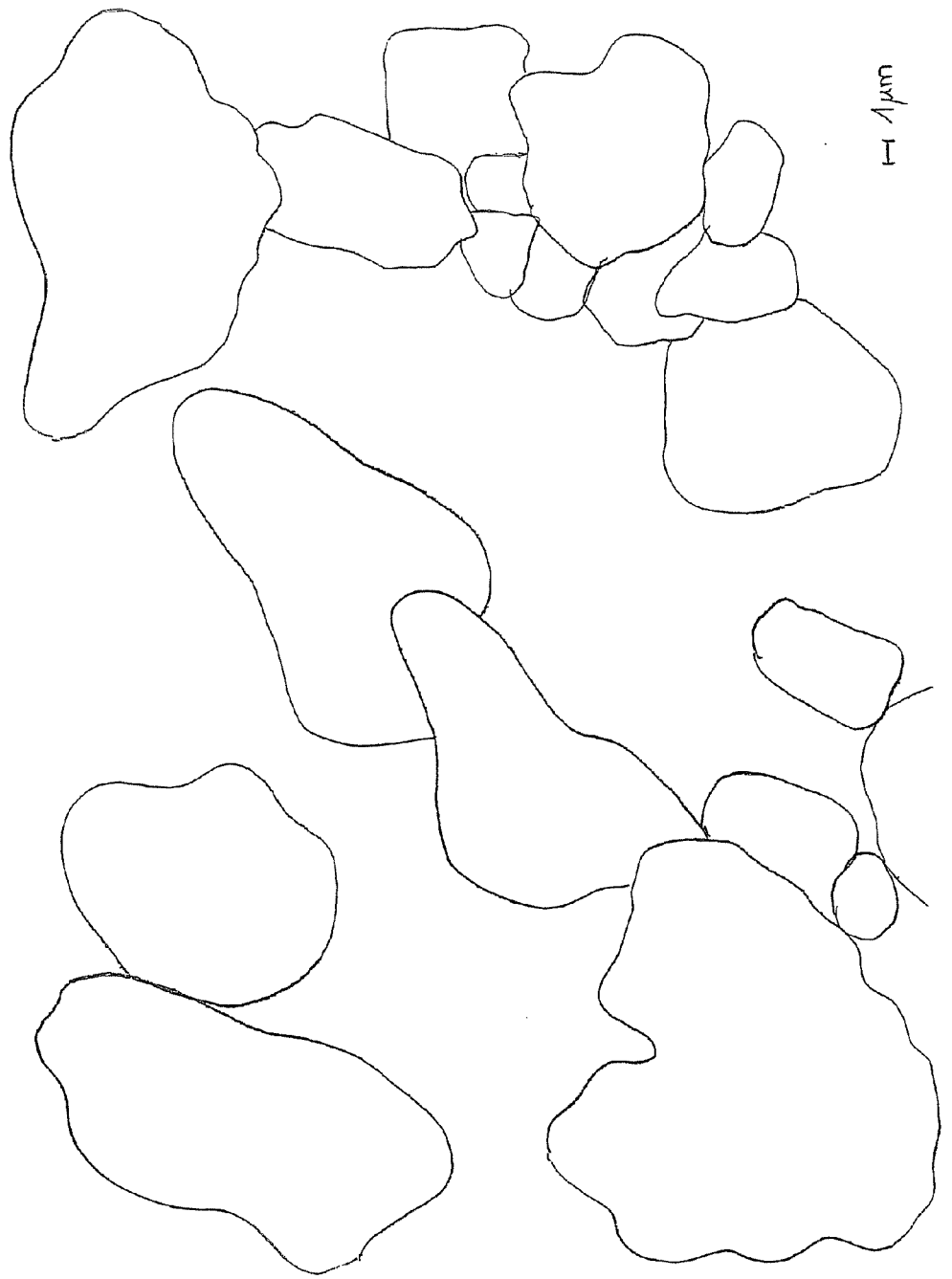

FIG. 1a shows an image of abrasive particles contained in a commonly available toothpaste. The image was taken by a commonly known scanning electron microscope (SEM). FIG. 1b shows a schematic drawing of these abrasive particles. As can be seen from these Figures, the abrasive particles composed of hydrated silica have sizes of several micrometers.

Figure 2A:
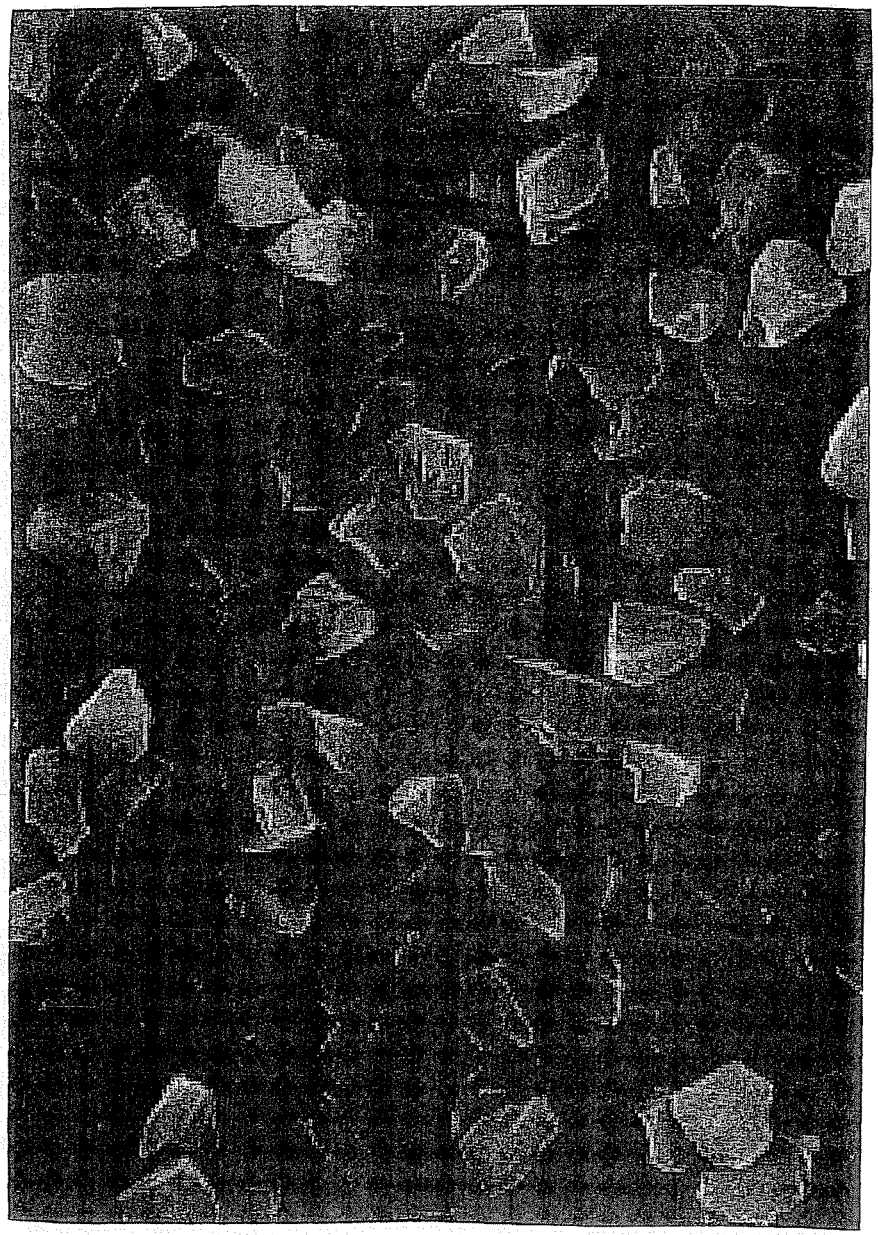
Figure 2B:
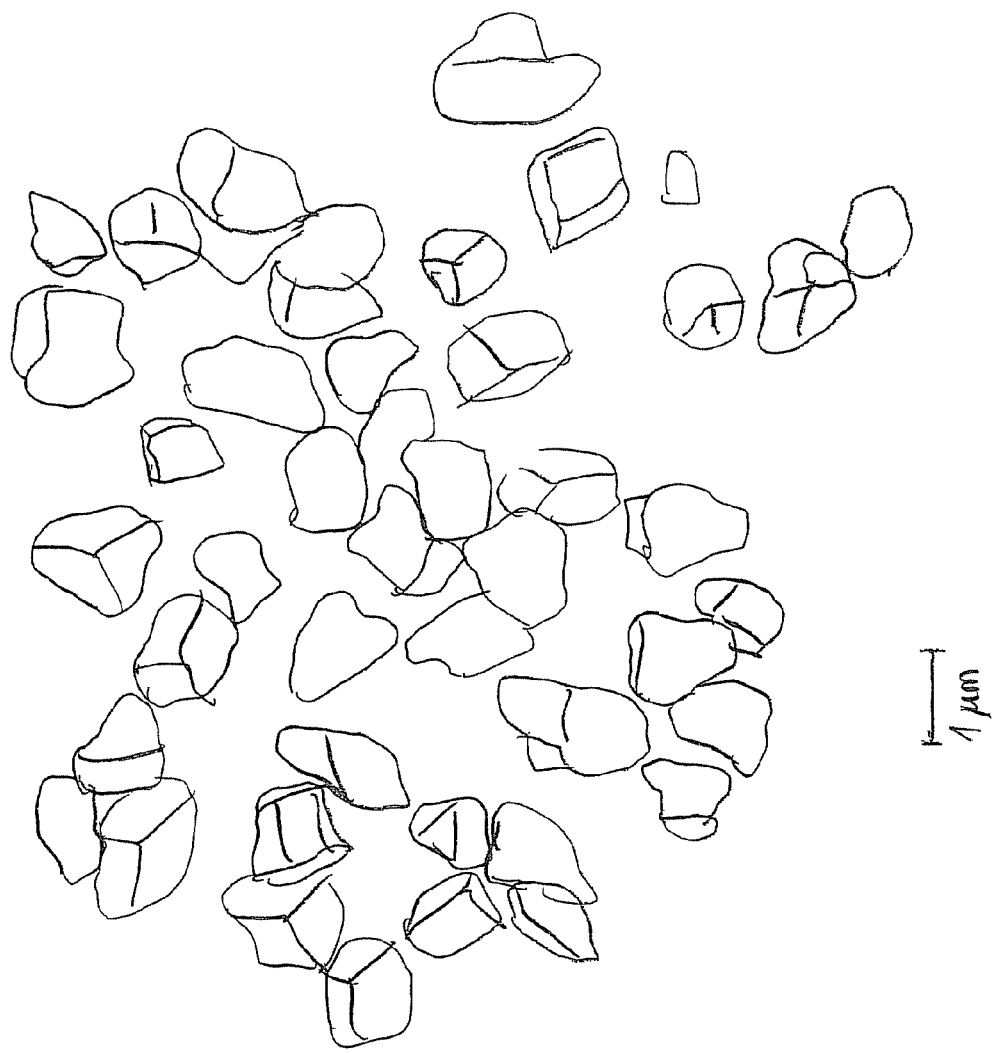

FIGS. 2a and 2b, on the other hand, show an SEM image and a schematic drawing, respectively, of the diamond particles contained in a toothpaste according to the invention. These diamond particles have a size distribution according to FIG. 3 (see below). Due to this reduced size with respect to the state of the art depicted in FIGS. 1a and 1b, the amount of material removed from the teeth during application of the toothpaste is significantly reduced.

Figure 3:
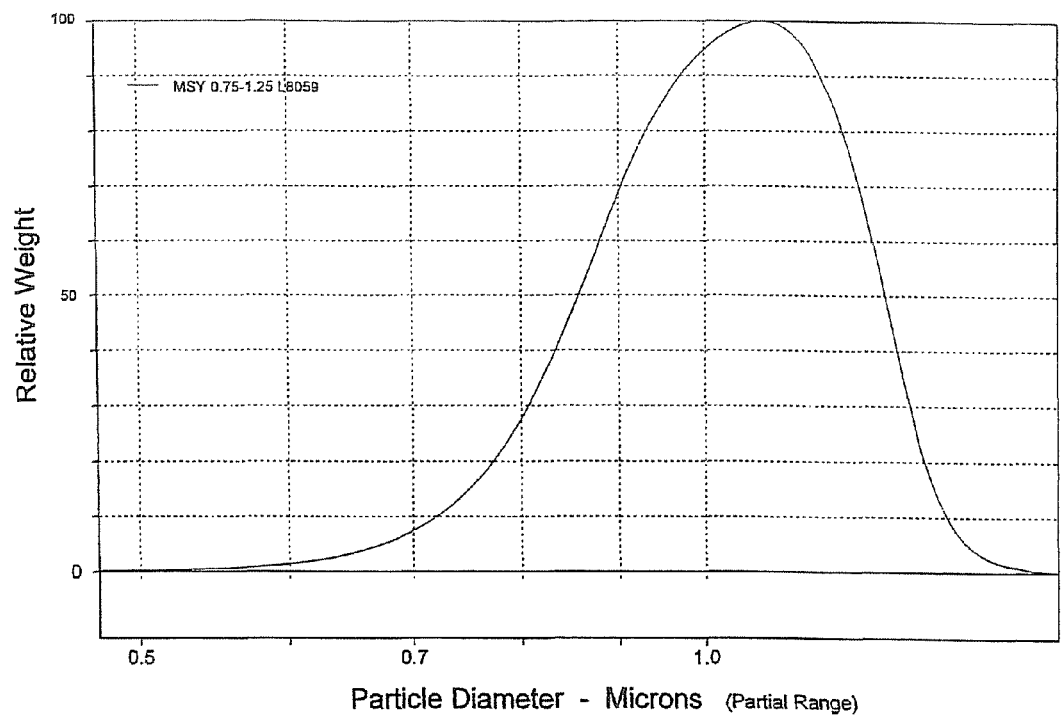
FIG. 3 shows the particle size distribution of the diamond particles of the toothpaste according to the invention.

FIG. 3 shows the particle size distribution of diamond particles contained in the toothpaste. This particle size distribution contains diamond particles having sizes in a size range from 0.75 µm to 1.5 µm. The particle size distribution contains also diamond particles below the lower end of the size range located at 0.75 µm. The particle size distribution may or may not contain diamond particles having sizes below 0.2 µm or even below 0.1 µm. However, according to preferred embodiments, the particle size distribution contains less than 0.005% by weight of diamond particles having sizes below 0.2 µm, wherein the percentage is taken with respect to the whole toothpaste. FIG. 3 is a semi-logarithmic plot showing a relative weight distribution, which is normalized such that the maximum in the semi-logarithmic plot corresponds to an ordinate value of 100. The distribution according to FIG. 3 has a maximum at 1.08 µm.

Figure 4:
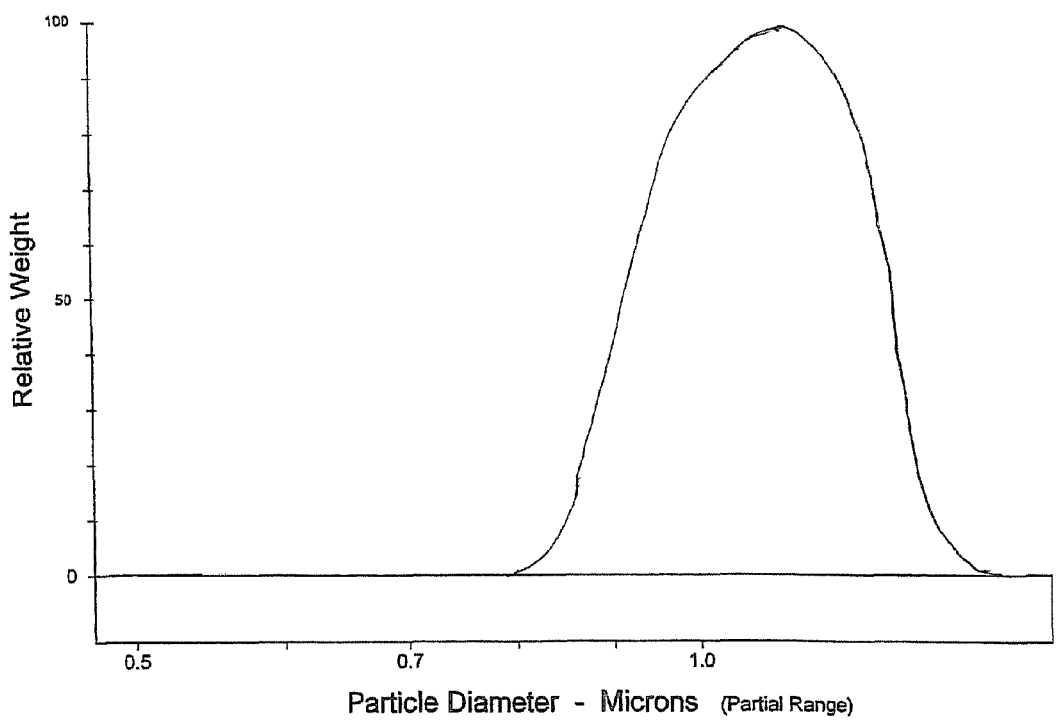
FIG. 4 shows the particle size distribution of the diamond particles of another toothpaste according to the invention.

FIG. 4 shows a diagram depicting the particle size distributions of the diamond particles in another toothpaste according to the invention. It is noted that this FIG. 4 also shows a relative weight distribution. The distribution of diamond particles according to FIG. 4 contains essentially only diamond particles within the size range between 0.75 µm and 1.5 µm, but less than 0.005% of diamond particles outside this size range (which cannot be graphically resolved in FIG. 4). This percentage is also taken with respect to the whole toothpaste.

Figure 5:
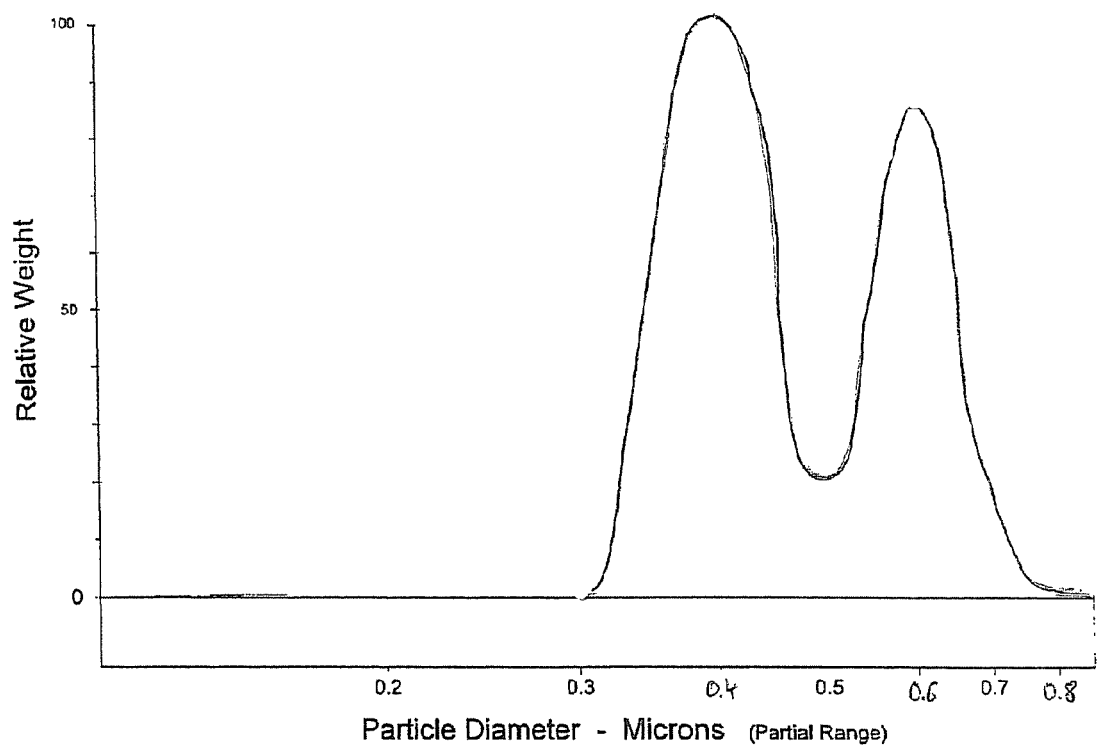
FIG. 5 shows the particle size distribution of the diamond particles of yet another toothpaste according to the invention.

FIG. 5 depicts the particle size distribution of the diamond particles in yet another toothpaste according to the invention. This diagram shows a relative weight distribution containing diamond particles having sizes between 0.3 µm and 0.8 µm. The distribution is a bimodal distribution having local maxima at 0.4 µm and 0.6 µm in the semi-logarithmic plot of FIG. 5. The size distribution contains less than 0.005% by weight of diamond particles having sizes below 0.2 µm, wherein these percentages are also taken with respect to the whole toothpaste.

Figure 6:
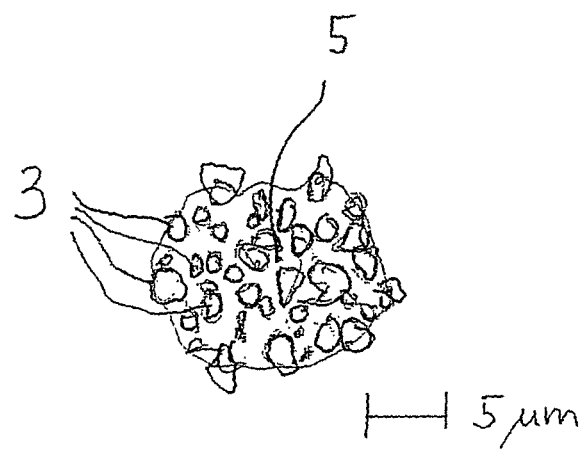
FIG. 6 shows a schematic drawing of a cluster with abrasive particles contained in a toothpaste according to the invention.

FIG. 6 shows a schematic drawing of a cluster 5 with diamond particles 3 contained in a toothpaste according to the invention. The diamond particles 3 are bonded by gelatine serving as a water-soluble binder and have sizes between 0.75 µm and 2.5 µm. At least 95% of the clusters within the toothpaste contain between 40% and 60% by volume of diamond particles 3. The manufacture of clusters containing particles bonded by gelatine is known per se, for example, from GB 1 460 069. Moreover, any other known technique for producing clusters may be applied, such as spray drying.

FIG. 7a shows a toothbrush 1 contained in the kit according to the invention. The toothbrush 1 comprises bristles 2. The bristles 2 consist of polyamide or polyester. They have a length of 11 mm and a diameter of 0.2 mm. The bristles 2 contain diamond particles 3 on their surfaces (cp. the enlarged view in FIG. 7b). The diamond particles 3 are bonded to the bristles 2 by a polyamide or polyester binder. For the manufacture, the bristles 2 are coated with a coating mixture containing the binder and the diamond particles 3.

Figure 7B:
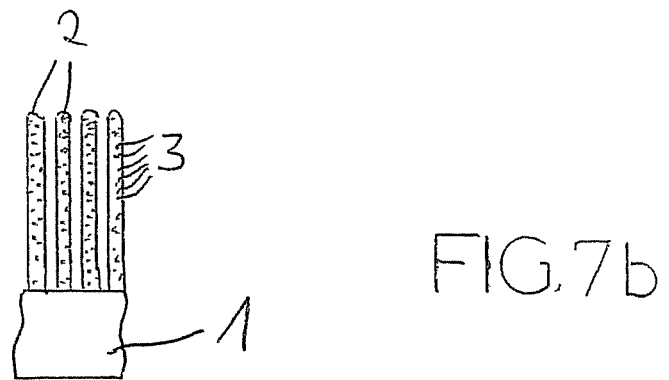

The diamond particles 3 of the bristles 2 have a median size of 2 µm and a standard deviation of 0.15 µm. Note that the abrasive particles 3 in FIG. 7b are not drawn to scale.

FIG. 8a shows another embodiment of a toothbrush 1 in an inventive kit of parts. As opposed to the toothbrush drawn in FIG. 7a, this toothbrush 1 does not contain any abrasive particles in its initial state. Instead, as shown in the enlarged view of FIG. 8b, the bristles 2 have a roughened surface having a surface roughness $R_{max}$ of 0.7 µm and a mean peak spacing according to ISO 4287 of 1 µm. The bristles 2 may be textured, for example, by sand blasting. The sand particles used in the manufacture by sand blasting may have sizes of 50 µm. Alternatively, the texture may be obtained by roughening the surface with an abrasive tool such as an abrasive disc or an abrasive brush.

The bristles 2 are roughened in such a way that the bristles 2 are capable of at least temporarily retaining diamond particles contained in the toothpaste of the kit. Thus, the bristles 2 are capable of retaining diamond particles in a range from about 0.3 µm to about 1 µm. These diamond particles may be mechanically retained by the bristles 2 by entering into recesses of the surface and by being clamped between neighboring elevations of the surface due the elasticity of the material of the bristles 2. FIG. 8c shows the bristles 2 of FIG. 8b which retain diamond particles 3, which have been picked up from a toothpaste according to the invention during the application of the toothpaste with the toothbrush 1.

FIG. 9 shows the particle size distribution of diamond particles contained in the toothpaste. This particle size distribution contains diamond particles having sizes in a first size range from 0.3 µm to 2.5 µm. Furthermore, this particle size distribution contains diamond particles having sizes in a second size range from 3.4 µm to 4.6 µm. FIG. 9 is a linear plot showing a relative weight distribution, which is normalized such that the maximum in the linear plot corresponds to an ordinate value of 100.

FIG. 10 shows a kit of parts 10 containing toothpaste with a first dental care product 11 and toothpaste with a second dental product 12. Both toothpastes are contained in a box 11, which is e.g. suitable for delivery of the kit of parts 10 to a buyer.

The first dental care product contains diamond particles with a median size of 1.2 µm. The second dental care product contains diamond particles with a median size of 4 µm and hydrogen peroxide as a tooth whitening agent.

EXAMPLE 1

Toothpaste

A first embodiment of a toothpaste according to the invention is prepared by admixing the following components by any technique known per se in the art, wherein the percentages are given by weight with respect to the total product:
60% of polyethylene glycol;
33.5% of sorbitol;
1.5% of sodium lauryl sulfate;
1.85% of spearmint;
2% of xanthan gum;
0.5% of sweetener;
0.15% of diamond particles according to the relative particle size distribution depicted in FIG. 3;
0.5% of sodium fluoride.

EXAMPLE 2

Toothpaste

A second embodiment of a toothpaste according to the invention is prepared by admixing the following components by any technique known per se in the art, wherein the percentages are given by weight with respect to the total product:
25% of glycerol;
25% of water;
43% of sorbitol;
1.5% of sodium lauryl sulfate;
1% of menthol;
3% of acacia gum;
0.5% of diamond particles according to the relative particle size distribution depicted in FIG. 3;
0.5% of titanium dioxide;
0.5% of sodium fluoride.

EXAMPLE 3

Toothpaste

A third embodiment of a toothpaste according to the invention is prepared by admixing the following components by any technique known per se in the art, wherein the percentages are given by weight with respect to the total product:
60% of glycerol;
33% of xylitol;
2% of sodium lauryl sulfate;
1.8% of peppermint;
2% of guar gum;
0.2% of diamond particles according to the relative particle size distribution depicted in FIG. 3;
0.25% of sodium fluoride;
0.25% of stannous fluoride;
0.5% of zinc citrate.

EXAMPLE 4

Toothpaste

A fourth embodiment of a toothpaste according to the invention is prepared by admixing the following components by any technique known per se in the art, wherein the percentages are given by weight with respect to the total product:
60% of glycerol;
33% of xylitol;
2% of sodium lauryl sulfate;
1.8% of peppermint;
2% of guar gum;
0.2% of diamond particles according to the relative particle size distribution depicted in FIG. 9;
0.25% of sodium fluoride;
0.25% of stannous fluoride;
0.5% of zinc citrate.

EXAMPLE 5

Toothpaste

A fifth embodiment of a toothpaste according to the invention is prepared by admixing the following components by any technique known per se in the art, wherein the percentages are given by weight with respect to the total product:
25% of glycerol;
25% of water;
43% of sorbitol;
1.4% of sodium lauryl sulfate;
1% of menthol;
3% of acacia gum;
0.5% of diamond particles according to the relative particle size distribution depicted in FIG. 3;
0.5% of titanium dioxide;
0.5% of sodium fluoride;
0.1% by weight of hydrogen peroxide

The invention claimed is:
1. A toothpaste comprising diamond particles having sizes within a first size range from 0.3 µm to 2.5 µm, wherein the amount of diamond particles having sizes within the first size range is at most 2% by weight of the toothpaste, wherein the toothpaste contains less than 0.025% by weight of diamond particles having sizes below 0.2 µm, and the toothpaste is suitable for home use by an unprofessional private consumer for his daily and/or weekly dental care.

2. A toothpaste according to claim 1, wherein the amount of diamond particles having sizes within the first size range is at least 0.0001% by weight of the toothpaste.

3. A toothpaste according to claim 1, wherein the total amount of all diamond particles in the toothpaste is less than 3% by weight of the toothpaste.

4. A toothpaste according to claim 1, wherein the toothpaste contains less than 0.005% by weight of diamond particles having sizes below 0.1 µm.

5. A toothpaste according to claim 1, wherein at least one active ingredient is bonded to at least a portion of the diamond particles.

6. A toothpaste according to claim 1, wherein the toothpaste contains clusters comprising diamond particles.

7. A toothpaste according to claim 6, wherein the toothpaste contains clusters having sizes between 1 µm and 100 µm.

8. A toothpaste according to claim 6, wherein at least 10% by weight of the diamond particles of the toothpaste are arranged in clusters.

9. A toothpaste according to claim 6, wherein at least 90% by weight of each cluster comprising diamond particles dissolves in water within a period of 5 minutes.

10. A toothpaste according to claim 1, wherein the toothpaste contains abrasive particles having sizes in a second size range between 2.6 µm and 10 µm.

11. A toothpaste according to claim 10, wherein the toothpaste contains abrasive particles having sizes in the second size range of at most 2% by weight of the toothpaste.

12. A toothpaste according to claim 1, wherein the toothpaste contains a tooth whitening agent.

13. A toothpaste according to claim 12, wherein the tooth whitening agent comprises at least one of the following: hydrogen peroxide, carbamide peroxide, pentanatriumtriphosphate, polyphosphates, pyrophosphates, citric acid, and papain.

14. A toothpaste according to claim 1, wherein the toothpaste has a Brookfield viscosity of at most 2,000,000 mPas.

* * * * *